United States Patent [19]

Llenado

[11] Patent Number: 4,565,647

[45] Date of Patent: * Jan. 21, 1986

[54] FOAMING SURFACTANT COMPOSITIONS

[75] Inventor: Ramon A. Llenado, West Chester, Ohio

[73] Assignee: The Procter & Gamble Company, Cincinnati, Ohio

[*] Notice: The portion of the term of this patent subsequent to Aug. 2, 2000 has been disclaimed.

[21] Appl. No.: 395,751

[22] Filed: Jul. 12, 1982

Related U.S. Application Data

[63] Continuation-in-part of Ser. No. 371,747, Apr. 26, 1982, abandoned, and Ser. No. 282,976, Jul. 13, 1981, abandoned.

[51] Int. Cl.$^4$ .................. B01F 17/02; B01F 17/12; B01F 17/56; B01J 13/00
[52] U.S. Cl. .......................... 252/354; 47/2; 209/20; 252/3; 252/8.5 C; 252/121; 252/174.17; 252/307; 252/353; 252/355; 252/555; 252/DIG. 10; 252/DIG. 13; 252/DIG. 14; 427/244
[58] Field of Search .............. 252/3, 307, 353, 174.17, 252/DIG. 13, DIG. 10, 354, 355

[56] References Cited

U.S. PATENT DOCUMENTS

| | | |
|---|---|---|
| 2,049,758 | 8/1936 | Bertsch et al. . |
| 2,390,507 | 12/1945 | Cantor . |
| 2,671,780 | 3/1954 | Gaver et al. . |
| 2,671,781 | 3/1954 | Gaver et al. . |
| 2,959,500 | 11/1960 | Schlapfer et al. . |
| 2,974,134 | 3/1961 | Pollitzer . |
| 3,092,618 | 6/1963 | Rosen et al. . |
| 3,219,656 | 11/1965 | Boettner . |
| 3,314,936 | 4/1967 | Ames . |
| 3,346,558 | 10/1967 | Roth . |
| 3,450,690 | 6/1969 | Gibbons et al. . |
| 3,547,828 | 12/1970 | Mansfield et al. . |
| 3,598,865 | 8/1971 | Lew . |
| 3,640,998 | 2/1972 | Mansfield et al. . |
| 3,721,633 | 3/1973 | Ranauto . |
| 3,737,426 | 6/1973 | Throckmorton et al. . |
| 3,772,269 | 11/1973 | Lew . |
| 3,839,318 | 10/1974 | Mansfield . |
| 3,842,847 | 10/1974 | Hewitt et al. ............... 252/DIG. 13 |
| 3,870,660 | 3/1975 | Paviak ....................... 252/DIG. 13 |
| 4,011,389 | 3/1977 | Langdon . |
| 4,088,583 | 5/1978 | Pyle et al. .................... 252/8.5 C X |
| 4,140,648 | 2/1979 | Thompson et al. .......... 252/305 X |
| 4,223,129 | 9/1980 | Roth et al. . |
| 4,240,921 | 12/1980 | Kaniecki . |
| 4,242,377 | 12/1980 | Roberts et al. ............... 252/305 X |
| 4,396,520 | 8/1983 | Payne et al. ............... 252/174.17 X |

FOREIGN PATENT DOCUMENTS

| | | |
|---|---|---|
| 593422 | 2/1934 | Fed. Rep. of Germany . |
| 3001064 | 7/1981 | Fed. Rep. of Germany . |

OTHER PUBLICATIONS

The Journal of The American Oil Chemist's Society, vol. 47, #5 (May 1980), pp. 162–167, Hughes et al., "Physical and Functional Properties of Some Higher Alkyl Polyglucosides".

The Journal of The American Chemical Society, vol. 60, (Sep. 1938), pp. 2076–2077, Noller et al.

Nature, vol. 197 (Mar. 16, 1963) Schram et al.

Several data sheets, Rohm & Haas Co., Material Safety Data Sheet, coded 6–1843; a page entitled "Manufacturing Specifications", Triton BG–10; A Specialty Chemicals Price List, schedule CS–429,25; a publication entitled The Qualitative and Quantitative Determination of Triton BG–10 in Bottle Washing Formulations, coded CS–400.

Y

*Primary Examiner*—Richard D. Lovering
*Attorney, Agent, or Firm*—Robert B. Aylor; Richard C. Witte; Thomas H. O'Flaherty

[57] ABSTRACT

Foaming compositions containing an alkylpolysaccharide surfactant and a sulfate, sulfonate and/or carboxylate cosurfactant and processes for utilizing foams containing these compositions.

10 Claims, No Drawings

FOAMING SURFACTANT COMPOSITIONS

CROSS REFERENCE TO RELATED APPLICATIONS

This is a continuation-in-part of my applications, Ser. No. 371,747, filed Apr. 26, 1982, and Ser. No. 282,976, filed July 13, 1981, both of which are now abandoned.

TECHNICAL FIELD

This invention relates to surfactant combinations which provide controllable aqueous foams. Such compositions can be used in any situation where foams are desirable, including the laundry, personal cleaning products, dishwashing, fire fighting, oil well drilling, ore beneficiation, solution mining, washing hair, preparation of foamed solid structures, etc.

DESCRIPTION OF THE PRIOR ART

Alkylpolyglycosides which are surfactants have been disclosed in U.S. Pat. Nos. 3,598,865; 3,721,633; and 3,772,269. These patents also disclose processes for making alkylpolyglycoside surfactants and built liquid detergent compositions containing these surfactants. U.S. Pat. No. 3,219,656 discloses alkylmonoglucosides and suggests their utility as foam stabilizers for other surfactants. Various polyglycoside surfactant structures and processes for making them are disclosed in U.S. Pat. Nos. 2,974,134; 3,640,998; 3,839,318; 3,314,936; 3,346,558; 4,011,389; 4,223,129. All of the above patents are incorporated herein by reference.

All percentages, parts and ratios used herein are by weight unless otherwise specified.

SUMMARY OF THE INVENTION

This invention relates to the discovery of certain combinations of surfactants which provide unusual foams. Specifically this invention relates to foaming compositions comprising (1) an alkylpolysaccharide surfactant having the formula $RO(R^1O)_tZ_x$ wherein Z is a moiety derived from a reducing saccharide containing from 5 to 6 carbon atoms, preferably a glucose, galactose, glucosyl, or galactosyl residue or mixtures thereof; R is a hydrophobic group selected from the group consisting of alkyl, alkyl phenyl, hydroxyalkyl phenyl or hydroxyalkyl alkyl groups or mixtures thereof in which said alkyl groups contain from about 8 to about 20 carbon atoms preferably from about 10 to about 16 carbon atoms, most preferably from about 12 to about 14 carbon atoms; $R^1$ contains from 2 to 4 carbon atoms, preferably ethylene, propylene and/or glyceryl, t is from 0 to about 30, preferably 0 to about 10, most preferably 0; wherein x is a number from about 1.5 to about 10, preferably 1.5 to 4, most preferably 1.6 to 2.7; and (2) an anionic cosurfactant which is a sulfate, sulfonate and/or carboxylate or mixtures thereof neutralized with one or more cationic moieties (M) to complete the formula, preferably the anionic cosurfactant has the formula $$R^9(SO_3)_y(COO)_zM_q;$$

wherein $R^9$ is an alkyl, alkylphenyl, hydroxyalkyl phenyl or hydroxyalkyl, or mixtures thereof, said alkyl groups containing from about 6 to about 30 carbon atoms, preferably about 10 to about 18 carbon atoms; y is a number from 0 to about 4, z is a number from 0 to about 4, y+z is at least 1, and M is a cationic moiety with q being selected to complete the formula, wherein the ratio of (2) to (1) is from about 1:10 to about 10:1 (i.e., 0.1 to 10.0) except that when the cosurfactant is an alkylbenzene sulfonate, the ratio of (2) to (1) is at least about 1:2 (i.e., at least about 0.5) and when y is 0 and z is one, the ratio of (2) to (1) is at least about 1:2 (i.e., at least about 0.5), and when the anionic cosurfactant does not contain a sulfonate or carboxylate group x must be from 1.5 to 3 and the alkylpolysaccharide surfactant must have a free fatty alcohol content of less than about 2% by weight of.

It has surprisingly been found that the cosurfactants interact with the alkylpolysaccharide surfactant of this invention to provide a relatively stable foam which is readily rinsed.

The invention also relates to the process of producing foams utilizing aqueous solutions containing from about 0.01% to about 95% of the mixed surfactants.

DESCRIPTION OF THE PREFERRED EMBODIMENTS

The Alkylpolysaccharide Surfactant

The alkylpolysaccharides are those having a hydrophobic group containing from about 8 to about 20 carbon atoms, preferably from about 10 to about 16 carbon atoms, most preferably from 12 to 14 carbon atoms, and a polysaccharide hydrophilic group containing from about 1.5 to about 10, preferably from 1.5 to 4, most preferably from 1.6 to 2.7 saccharide units (e.g., galactoside, glucoside, fructoside, glucosyl, fructosyl and/or galactosyl units). Mixtures of saccharide moieties may be used in the alkyl polysaccharide surfactants. The number x indicates the number of saccharide units in a particular alkylpolysaccharide surfactant. For a particular alkylpolysaccharide molecule x can only assume integral values. In any physical sample of alkylpolysaccharide surfactants there will in general be molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactosides, fructosides, etc., is preferred. In the preferred product the additional saccharide units are predominately attached to the previous saccharide unit's 2-position. Attachment through the 3-, 4-, and 6-positions can also occur.

Optionally and less desirably there can be a polyalkoxide chain joining the hydrophobic moiety (R) and the polysaccharide-chain. The preferred alkoxide moiety is ethoxide.

Typical hydrophobic groups include alkyl groups, either saturated or unsaturated, branched or unbranched containing from about 8 to about 20, preferably from about 10 to about 16 carbon atoms. Preferably, the alkyl group is a straight chain saturated alkyl group. The alkyl group can contain up to 3 hydroxy groups and/or the polyalkoxide chain can contain up to about 30, preferably less than 10, most preferably 0, alkoxide moieties.

Suitable alkyl polysaccharides are decyl, dodecyl, tetradecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkylmonosaccharides are relatively less soluble in water than the higher alkylpolysaccharides. When used in admixture with alkylpolysaccharides, the alkylmonosaccharides are solubilized to some extent. The use of alkylmonosaccharides in admixture with alkylpolysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$R^2O(C_nH_{2n}O)_t(Z)_x$$

wherein Z is derived from glucose, $R^2$ is a hydrophobic group selected from the group consisting of alkyl, alkylphenyl, hydroxyalkyl, hydroxyalkylphenyl, and mixtures thereof in which said alkyl groups contain from about 10 to about 18, preferably from 12 to 14 carbon atoms; n is 2 or 3, preferably 2, t is from 0 to about 10, preferably 0; and x is from 1.5 to about 8, preferably from 1.5 to 4, most preferably from 1.6 to 2.7. To prepare these compounds a long chain alcohol ($R^2OH$) can be reacted with glucose, in the presence of an acid catalyst to form the desired glucoside. Alternatively the alkylpolyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R^2OH$) to displace the short chain alcohol and obtain the desired alkylpolyglucoside. If this two step procedure is used, the short chain alkylglucoside content of the final alkylpolyglucoside material should be less than 50%, preferably less than 10%, more preferably less than 5%, most preferably 0% of the alkylpolyglucoside.

The amount of unreacted alcohol (the free fatty alcohol content) in the desired alkylpolysaccharide surfactant is preferably less than about 2%, more preferably less than about 0.5% by weight of the total of the alkyl polysaccharide plus unreacted alcohol. The amount of alkylmonosaccharide is about 20% to about 70%, preferably 30% to 60%, most preferably 30% to 50% by weight of the total of the alkylpolysaccharide. For some uses it is desirable to have the alkylmonosaccharide content less than about 10%.

As used herein, "alkylpolysaccharide surfactant" is intended to represent both the preferred glucose and galactose derived surfactants and the less preferred alkylpolysaccharide surfactants. Throughout this specification, "alkylpolyglucoside" is used to include alkylpolyglycosides because the stereo chemistry of the saccharide moiety is changed during the preparation reaction.

THE ANIONIC COSURFACTANTS

Anionic cosurfactants can be selected from the group consisting of sulfates, sulfonates, carboxylates and mixtures thereof. The cosurfactants are neutralized with a cationic moiety or moieties selected from the group consisting of alkali metal, e.g. sodium or potassium, alkaline earth metal, e.g. calcium or magnesium, ammonium, subtituted ammonium, including mono-, di-, or tri-, ethanolammonium cations. Mixtures of cations can be desirable. The anionic cosurfactants useful in the present invention all have detergent properties and are all water soluble or dispersible in water.

Alkylbenzene Sulfonates

One of the preferred cosurfactants for use in this invention is an alkylbenzene sulfonate. The alkyl group can be either saturated or unsaturated, branched or straight chain and is optionally substituted with a hydroxy group. Middle phenyl positions are generally preferred for volume of foaming in light soil conditions. However, in heavier soil conditions phenyl attachment at the 1- or 2-position is preferred.

The preferred alkylbenzene sulfonates contain a straight alkyl chain containing from about 9 to about 25 carbon atoms, preferably from about 10 to about 13 carbon atoms, and the cation is sodium, potassium, ammonium, mono-, di-, or triethanolammonium, calcium or magnesium and mixtures thereof. Magnesium is the preferred cationic moiety. These same cations are preferred for other anionic surfactants and ingredients. The magnesium alkylbenzene sulfonates where the phenyl group is attached near the middle of the alkyl chain are surprisingly better than the ones with the phenyl near the end of the chain when the polysaccharide chain averages greater than about 3 saccharide units. Suitable alkylbenzene sulfonates include $C_{11}$ alkylbenzene sulfonates with low 2-phenyl content.

The alkylbenzene sulfonate cosurfactant is desirable in the foaming compositions of the invention since the foams produced therewith are exceptionally stable, have a large volume, rinse quickly, and do not have a "slippery" feel. These compositions are particularly desirable for industrial and commercial processes as discussed hereinafter. The volume of foam produced using the alkylbenzene sulfonate cosurfactant is larger than for any other cosurfactant.

Soap

Other preferred cosurfactants for use in this invention are carboxylates, e.g. fatty acid soaps and similar surfactants. The soaps can be saturated or unsaturated and can contain various substituents such as hydroxy groups and alpha-sulfonate groups. Preferably, the hydrophobic portion of the soap is a straight chain saturated or unsaturated hydrocarbon. The hydrophobic portion of the soap usually contains from about 6 to about 30 carbon atoms, preferably from about 10 to about 18 carbon atoms. The use of carboxylate cosurfactants is especially valuable since the alkylpolysaccharide surfactants are exceptional lime soap dispersers.

The cationic moiety (M) for carboxylate cosurfactants is selected from the group consisting of alkali metal, for example, sodium or potassium, alkaline earth metal, for example, calcium or magnesium, ammonium, or substituted ammonium, including mono-, di-, or triethanolammonium cations. Mixtures of cations can be desirable.

In addition to the preferred alkylbenzene sulfonate and soap cosurfactants many other surfactants which contain sulfonate or carboxylate groups can be used in the foaming compositions of the invention. Generally the use of these latter cosurfactants produces less foam volume than does the use of the preferred cosurfactants. However, the alkylpolysaccharide surfactant stabilizes the foams which are produced and allows the foams to be rinsed more quickly.

One group of cosurfactants that are of interest because of their superior detergency are the zwitterionic detergents which contain both a cationic group, either ammonium, phosphonium, sulfonium or mixtures thereof and a sulfonate or carboxylate group. Preferably there are at least about four atoms separating the cationic and anionic groups. Suitable zwitterionic surfactants are disclosed in U.S. Pat. Nos. 4,159,277; 3,928,251; 3,925,262; 3,929,678; 3,227,749; 3,539,521; 3,383,321; 3,390,094; and 3,239,560, incorporated herein by reference. Such cosurfactants are especially desirable for shampoos.

Another group of cosurfactants are the amphoteric detergents which have the same general structure as the zwitterionic surfactants but with an amine group instead of the quaternary ammonium group.

Yet other cosurfactants are the alkyl (paraffin or olefin) sulfonates, preferably with a more central hydrophilic group, containing from about 6 to about 30 carbon atoms. Compositions containing these cosurfactants produce the least volume of foam, if that is desired. The hydrophobic group can contain up to about 10 hydroxy groups and/or ether linkages. Examples include $C_{14-5}$ paraffin sulfonates and $C_{14-16}$ olefin sulfonates.

Still another cosurfactant is a soap structure containing up to about 10 ether linkages in the chain and from about 1 to about 4 carbon atoms between ether linkages with from about 6 to about 30 carbon atoms in a terminal portion containing no ether linkages.

The preferred alkylpolyglucosides that contain an average of from 1.5 to 4 glucoside units, preferably from 1.6 to 2.7 glucoside units; less than about 50% short chain alkylpolyglucosides; less than about 10%, preferably less than about 2%, most preferably less than about 0.5% unreacted fatty alcohol, increase the sudsing ability of conventional sulfate detergent cosurfactants, especially alkyl sulfate and alkyl polyether sulfate cosurfactants having the formula:

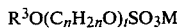
$R^3O(C_nH_{2n}O)_tSO_3M$ wherein $R^3$ is an alkyl or hydroxyalkyl group containing from about 8 to about 18 carbon atoms, n is 2 or 3, t can vary from 0 to about 30, and M is a cationic moiety as defined above, the cosurfactant being water soluble or dispersible.

A preferred foaming composition of the invention herein comprises (1) an alkylpolysaccharide surfactant having the formula $RO(R^1O)_t(Z)_x$ wherein Z is a moiety derived from a reducing saccharide containing from 5 to 6 carbon atoms and wherein R is a hydrophobic group selected from the group consisting of alkyl, alkylphenyl, hydroxyalkylphenyl or hydroxyalkyl groups or mixtures thereof in which said alkyl groups contain from about 8 to about 18 carbon atoms; $R^1$ contains from 2 to about 4 carbon atoms; t is from 0 to about 30; and x is a number from about 1.5 to about 10, preferably 1.5 to 4, most preferably 1.6 to 2.7; and (2) a mixture of cosurfactants neutralized with one or more cationic moieties consisting essentially of:

(a) from about 1% to about 95% preferably about 10% to about 50% of a water soluble alkylbenzene sulfonate cosurfactant in which the alkyl group contains from about 10 to about 13 carbon atoms, and (b) from about 5% to about 99%, preferably 50-90% of a cosurfactant selected from the group consisting of an alkyl glyceryl ether sulfonate in which the alkyl group contains from about 8 to about 18 carbon atoms, an alpha-olefin sulfonate in which the olefin group contains from about 10 to about 18 carbon atoms, an alkyl polyethoxylate carboxylate in which the alkyl group contains from about 10 to about 18 carbon atoms, and the polyethoxylate chain contains from about 2 to about 6 ethoxylate groups, and mixtures thereof.

Such compositions have improved suds mileage as compared to compositions containing only the alkyl benzene sulfonate cosurfactant and the alkylpolysaccharide surfactant.

Another preferred embodiment of a foaming composition of the invention herein comprises (1) an alkylpolysaccharide surfactant having the formula $RO(R^1O)_t(Z)_x$ wherein Z is a moiety derived from a reducing saccharide containing from 5 to 6 carbon atoms and wherein R is a hydrophobic group selected from the group consisting of alkyl, alkylphenyl, hydroxyalkylphenyl or hydroxyalkyl groups or mixtures thereof in which said alkyl groups contain from about 8 to about 18 carbon atoms; $R^1$ contains from 2 to about 4 carbon atoms; t is from 0 to about 30; and x is a number from about 1.5 to about 10;

(2) an anionic cosurfactant selected from the group consisting of sulfates, sulfonates, carboxylates and mixtures thereof neutralized with one or more cationic moieties M to complete the formula, the ratio of (2) to (1) being from about 1:10 to about 10:1; and (3) from about 2% to about 10% of an auxiliary foam booster selected from the group consisting of:

(a) amides having the formula

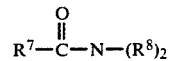

wherein $R^7$ is an alkyl group containing from about 8 to about 18 carbon atoms, preferably about 12 to about 14 carbon atoms and each $R^8$ is the same or different and is selected from the group consisting of hydrogen, $C_{1-3}$ alkyl, $C_{1-3}$ alkanol, and $-(C_2H_4O-)_{1-4}H$ groups and mixtures thereof;

(b) amine oxides having the formula:

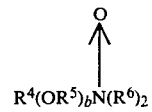

wherein $R^4$ is an alkyl group containing from about 8 to about 18 carbon atoms, preferably from 12 to 14 carbon atoms, each $R^5$ contains two or three carbon atoms, b is from 0 to about 30, each $R^6$ is the same or different and is selected from the group consisting of $C_{1-3}$ alkyl, $C_{1-3}$ alkanol, and $-(C_2H_4O)_{1-6}H$ groups and mixtures thereof; and (c) mixtures thereof.

Such compositions provide superior grease/oil removal and suds mileage.

Preferred anionic cosurfactants are alkylbenzene sulfonate, alpha-olefin sulfonate, alkylsulfates, alkylpolyethoxylate sulfates and paraffin sulfonates and mixtures thereof. The cationic moieties are selected from the group consisting of sodium, potassium, ammonium, monoethanolammonium, diethanolammonium, triethanolammonium, calcium, magnesium and mixtures thereof.

Preferred compositions of this embodiment of the invention comprise from 1% to about 95%, preferably 5% to about 50% of an alkylpolysaccharide surfactant in which the alkyl group contains from 12 to 14 carbon atoms, x is from 1.5 to 4, more preferably 1.6 to 2.7; from 1% to about 95%, preferably from about 10% to about 50% of an anionic cosurfactant neutralized with one or more cationic moieties and which is a mixture of (1) from 1% to about 95%, preferably from about 5% to about 50% of an alkyl benzene sulfonate in which the alkyl group contains from about 8 to about 13 carbon atoms or an alpha-olefin sulfonate in which the olefin group contains from about 10 to about 18 carbon atoms, or mixtures thereof; and (2) from 1% to about 95%, preferably from about 5% to about 50% of an alkyl polyethoxylate sulfate in which the alkyl group contains from about 8 to about 18 carbon atoms, preferably from 12 to 14 carbon atoms and from about one to about six ethoxylate moieties and wherein from about 1% to about 100%, preferably from about 10% to about 80% of the cationic moieties are magnesium: and wherein the auxiliary foam booster is an amide.

Another preferred foaming composition of the invention herein is an agglomerated light duty detergent granule composition comprising (1) from about 5% to about 60%, preferably from 10% to about 20% of an alkylpolysaccharide surfactant having the formula $RO(R^1O)_t(Z)_x$ wherein Z is a moiety derived from a reducing saccharide moiety containing from 5 to 6 carbon atoms and wherein R is a hydrophobic group selected from the group consisting of alkyl, alkylphenyl, hydroxyalkylphenyl or hydroxyalkyl grups or mixtures thereof in which said alkyl groups contain from about 8 to about 18 carbon atoms, preferably from 12 to 14 carbon atoms; $R^1$ contains from 2 to about 4 carbon atoms; t is from 0 to about 30; and x is a number from about 1.5 to about 10, preferably 1.5 to 4, most preferably 1.6 to 2.7;

(2) from about 5% to about 60% of an alkyl benzene sulfonate cosurfactant in which the alkyl group contains from about 10 to about 13 carbon atoms, said alkyl benzene sulfonate neutralized with one or more cationic moieties (M) to balance the formula;

(3) from about 5% to about 60%, preferably from about 10% to about 20% of an alkylpolyethoxylate sulfate cosurfactant in which the alkyl group contains from about 10 to about 16 carbon atoms and in which there are from 1 to about 6 ethoxylate groups, said alkylpolyethoxylate sulfate neutralized with one or more cationic moieties M to complete the formula.

(4) from about 5% to about 80% of a water soluble inorganic salt selected from the group consisting of sodium and potassium sulfates, chlorides, carbonates, phosphates, and mixtures thereof.

The Processes

Mixtures of alkylbenzene sulfonate and/or the soap cosurfactant and the alkylpolysaccharide surfactant can be used at levels of from about 0.01% to about 95%, in ratios of cosurfactant to alkylpolysaccharide of from about 10:1 to about 1:10, in water with agitation to provide foams. These foams are relatively stable and, if not disturbed, can exist for several days. Furthermore, the foam has structural integrity and does not spread out. The foams prepared using mixtures of alkylbenzene sulfonate and the alkylpolysaccharide are unique in that they do not have a "slippery" feel. All of the foams rinse quickly.

The unusual properties of the foams of this invention make them valuable for use not only in soap bars, bubble baths, shaving creams, laundry, dishwashing, and washing hair, where a good volume of stable suds and quick rinsability are desirable, but also in a large number of fields unrelated to detergency.

The compositions and processes of this invention are particularly valuable for use in the "foam" or "mist" well drilling processes in which the foam is used to carry water and/or soil particles to the surface of the bore hole. A description of such a drilling method can be found in U.S. Pat. Nos. 3,303,896; 3,111,178; 3,130,798; and 3,215,200; incorporated herein by reference. In such a process, the surfactants are present at a level of from about 0.01% to about 5%, preferably from about 0.01% to about 2%, most preferably from about 0.05% to about 0.5%. The preferred cosurfactant is an alkylbenzene sulfonate.

The compositions and processes of this invention are also of considerable value in fire fighting or fire prevention processes where a stable foam is used to extinguish a flame or sparks by cutting off the oxygen supply. This includes fire fighting and foaming runways for crash-landings as disclosed in U.S. Pat. Nos. 2,514,310; 3,186,943; 3,422,011; 3,457,172; 3,479,285; and 3,541,010, incorporated herein by reference. Concentrations of from about 0.1% to about 5% are useful.

The compositions and processes of this invention are also especially valuable in the field of preparing gypsum board, plastic, and resin foams. The foams of this invention provide a stable relatively thick structure permitting solidification of the resins, plastics, cellulosic particles, etc., into stable foam structures having light densities, thick cell walls and good structural integrity. Examples of forming processes which utilize foaming agents are described in U.S. Pat. Nos. 3,669,898; 4,907,982; 4,423,720; and 4,423,720, incorporated herein by reference.

The flotation of minerals so as to concentrate the mineral values, e.g., in the foam (beneficiation), can be carried out advantageously using the compositions and processes of this invention. Such processes are described in U.S. Pat. Nos. 4,147,644; 4,139,482; 4,139,481; 4,138,350; 4,090,972; and 3,640,862, incorporated herein by reference.

A special advantage of the compositions and processes of this invention involves making use of their exceptional stability to provide temporary insulation for plants when freezing conditions are expected. An alkyl-benzene sulfonate is the preferred cosurfactant and the foam can be applied to the foliage etc., of the plants. Such a process is disclosed in U.S. Pat. No. 3,669,898, incorporated herein by reference.

The range of utilities which are possible with the compositions and processes of this invention include all of the above and many more.

Typical compositions for use as light duty liquid detergent compositions in washing dishes comprise from about 5% to about 50%, preferably from about 10% to about 40% of the mixture of surfactants disclosed hereinbefore. From about 1% to about 50% of a solvent selected from the group consisting of $C_{1-3}$ alkanols, $C_{1-3}$ alkanolamines, $C_{2-4}$ polyols, mixtures thereof, and the balance water. It is a special advantage of the compositions of this invention that they can be made in concentrated form (up to about 50% by wt. of the mixture of surfactants) with only very low levels of organic solvents and without the addition of expensive hydrotropic materials. Additional suds boosters or builders such as trialkyl amine oxides and fatty acid amides can also be used in amounts up to about 20%. Fatty alcohols should not be used.

Shampoo compositions comprise from about 1% to about 95%, preferably from about 5% to about 20% of the mixture of surfactants mentioned hereinbefore, from about 1% to about 5% of an alkanol amide, from about 0.5% to about 3% of a polymeric thickener, and the balance water. It is a special advantage of the shampoos that they rinse quickly and readily.

Additional Ingredients

The compositions and processes of this invention can utilize other compatible ingredients, including other surfactants, in addition to the mixture of surfactants herein disclosed. In detergent compositions the compositions can contain any of the well known ingredients including minor amounts of other surfactants, detergency builders, soil suspending agents, brighteners, abrasives, dyes, fabric conditioning agents, hair conditioning agents, hydrotropes, solvents, fillers, clays, perfumes, etc. Suitable ingredients are disclosed in U.S. Pat. No. 4,166,039—Wise; U.S. Pat. No. 4,157,978—Llenado; U.S. Pat. No. 4,056,481—Tate; U.S. Pat. No. 4,049,586—Collier; U.S. Pat. No. 4,035,257—Cherney; U.S. Pat. No. 4,019,998—Benson et al; U.S. Pat. No. 4,000,080—Bartolotta et al; and U.S. Pat. No. 3,983,078—Collins, incorporated herein by reference. The shampoo compositions of this invention can contain any of the additional ingredients known to the art to be suitable for use in shampoos. Listings of suitable additional ingredients, including low levels of other surfactants can be found in U.S. Pat. Nos. 4,089,945; 3,987,161; and 3,962,418, incorporated herein by reference.

Of special interest are ingredients which modify the feel of aqueous solutions containing the foaming compositions of this invention. For example, raising the pH to above about 8.5 by alkaline materials or incorporating the tertiary alcohols of the U.S. patent application of Jones et al, Ser. No. 193,050, filed Oct. 2, 1980, now abandoned, said application being incorporated by reference. Such ingredients are desirable for some consumers since the solutions do not have the normal "soapy" feel associated with surfactant solutions.

The following nonlimiting examples illustrate the foaming compositions of the present invention.

EXAMPLE I

Relative Volume of Suds Comparison and Consumer Preference

|  | A Generic Commercial Product U.S. Crystal White ® Weight % | B Premium Commercial Product U.S. Palmolive ® Weight % | C Product of the Invention Weight % |
|---|---|---|---|
| FORMULA |  |  |  |
| Sodium $C_{11.8}$ alkyl benzene sulfonate | 10.5 | 18.0 | 18.0 |
| $C_{12-13}$ alkylpolyglucoside$_{2-3}$ (>2% free fatty alcohol) | — | — | 12.0 |
| Sodium $C_{14-15}$ alkyl polyethoxylate$_3$ sulfate | 5.5 | 12.0 | — |
| Balance of formula inc. water | 84.0 | 70.0 | 70.0 |
| SUDSING |  |  |  |
| Relative Volume of Suds (ml) 0.2% solutions | 110 | 125 | 220 |
| CONSUMER TEST |  |  |  |
| Overall preference, % | 10 | 18 | 23 |
| Favorable sudsing comments, % | 74 | 85 | 90 |
| Favorable rinsing comments, % | 3 | 6 | 10 |

The foaming composition of the invention is superior to a representative generic product and at least equivalent to a representative premium commercial product and is preferred by consumers for rinsing reasons. The test involved 50 consumers washing soiled dishes in the test solutions. The consumers wore rubber gloves during the test. The differences are significant at the 95% confidence level for the invention over the generic product.

The relative volume of suds in ml. is determined by the following test procedure:

100 ml of the test solution at 115° F. is placed in a 500 ml graduated cyliner: the solution is agitated by repeated inversion of the graduated cylinder until the amount of suds in the cylinder does not increase with further agitation. Suds height is measured directly on the cylinder scale making allowance for the height of liquid remaining in the cylinder. The test solution is made by adding the test product to water having a hardness of 7 gr. per U.S. gallon (Ca/Mg=3/1).

EXAMPLE II

LAS Suds Boosting

| Wt. % of: | A | B | C | D | E | F | G |
|---|---|---|---|---|---|---|---|
| Sodium $C_{11.8}$ alkylbenzene sulfonate | 0 | 20 | 40 | 50 | 60 | 80 | 100 |
| $C_{12-15}$ alkylpoly$_{2-3}$ glucoside | 100 | 80 | 60 | 50 | 40 | 20 | 0 |
| Relative Volume of suds (ml) | 140 | 220 | 280 | 300 | 310 | 300 | 240 |

The suds (foam) were generated as described in Ex. I using 300 ppm of the surfactant mixtures in city water (~9 grains per gallon). The results clearly show the sudsing synergism for ratios greater than about 1:2, i.e. for the foaming composition of the invention herein.

EXAMPLE III

Soap Suds Boosting

| Wt. % of: | A | B | C | D | E | F |
|---|---|---|---|---|---|---|
| Sodium oleate | 0 | 20 | 40 | 60 | 80 | 100 |
| $C_{12-15}$ alkylpoly$_{2-3}$ glucoside | 100 | 80 | 60 | 40 | 20 | 0 |
| Relative Volume of suds (ml.) | 160 | 270 | 280 | 300 | 310 | 260 |

The suds were generated as in Ex. I using 500 ppm. of the surfactant mixtures. This data clearly indicates the sudsing synergism for the foaming composition of the invention herein.

EXAMPLE IV

Foaming with Soap Effect of Hardness on Relative Volume of Suds

|  | grains hardness | | | |
|---|---|---|---|---|
|  | 0 | 2 | 4 | 6 |
| Sodium oleate | 225 | 10 | 0 | 0 |
| Sodium oleate plus $C_{12-15}$ alkylpoly$_{2-3}$ glucoside (3:2 ratio) | 360 | 100 | 55 | 10 |

The suds were generated as in Ex. I using 500 ppm. of the surfactant mixtures.

EXAMPLE V

Alkyl Polyglucoside ($C_{12-15}$ alkylpoly$_{2-3}$glucoside) Suds Boosting for the Following Representative Cosurfactants (3:2 ratio; 500 ppm)

|  | % increase in foaming |
|---|---|
| Sodium $C_{11.8}$ alkylbenzene sulfonate | 100–150 |
| Sodium oleate | 50–75 |
| 3-[N—coconutalkyl-N,N—dimethyl]-2-hydroxy-1-sulfonate | 40–60 |
| Sodium $C_{14-15}$ olefin sulfonate | 20–40 |
| Sodium coconut alkyl sulfate | 10–30 |
| Sodium coconut alkyl polyethoxylate$_3$ sulfate | 0–20 |

The above data clearly demonstrate the criticality of utilizing a carboxylate or sulfonate anionic detergent cosurfactant for sudsing synergism with the alkyl polyglucoside surfactant.

EXAMPLE VI

Glucoside Chain Length Criticality

40:60 wt. ratio of $C_{12-15}$ alkyl polyglucoside to sodium $C_{12}$ alkylbenzene sulfonate (500 ppm. concentration) where the glucoside portion is:

|  | Relative Volume of Suds (ml) |
|---|---|
| Monoglucoside | 180 |
| Diglucoside | 240 |
| Pentaglucoside | 260 |
| Decaglucoside | 170 |
| Sodium $C_{11.8}$ alkylbenzene sulfonate alone | 160 |

"Diglucoside" etc. indicates the average glucoside chain length in the sample is two, etc. As can be seen from the above, significant synergism is obtained only with 1.5 or more glucoside units and preferably less than about 10, more preferably less than about 8 glucoside units.

EXAMPLE VII

Alkylbenzene sulfonates (LAS) Homologs/phenyl-position (3:2 ratio; 500 ppm)

|  | Relative Volume of Suds (ml) |
|---|---|
| Ex. II's alkylpolyglucoside plus: |  |
| Sodium $C_{11}$ LAS, high 2-phenyl | 210 |
| Sodium $C_{11}$ LAS, low 2-phenyl | 250 |
| Sodium $C_{12}$ LAS, high 2-phenyl | 225 |
| Sodium $C_{12}$ LAS, low 2-phenyl | 225 |
| Sodium $C_{14}$ LAS, high 2-phenyl | 210 |
| Sodium $C_{14}$ LAS, low 2-phenyl | 215 |

As can be seen from the above, in general $C_{11}$, low 2-phenyl LAS is preferred for sudsing.

EXAMPLE VIII

Suds Boosting of Alkyl Polyglucosides and Effect of Soil

|  | Relative Volume of Suds (ml) | | |
|---|---|---|---|
|  | Without Soil | With Soil* | |
|  |  | 0.5% | 1.0% |
| 0.2% aqueous solution of a detergent composition formulated with: |  |  |  |
| 15% sodium $C_{11.8}$ alkylbenzene sulfonate ($C_{11.8}$ LAS) | 120 | 50 | 25 |
| 15% $C_{11.8}$ LAS + 12% Ex. II's alkyl polyglucoside | 310 | 130 | 70 |
| 30% $C_{11.8}$ LAS | 190 | 140 | 100 |
| 20% $C_{11.8}$ LAS + 12% Ex. I's alkylpolyglucoside | 380 | 170 | 180 |

*Test method of Ex. 1 modified by adding to the test solution the indicated amount of soil. % is wt. % of test solution.

The soil is a 44%/56% by weight mixture of Fluffo ® and PREP ® both of which products are available in the United States from The Proctor & Gamble Company.

As can be seen from the above, the benefit for the invention is even more remarkable when soil is present.

EXAMPLE IX

|  | Relative Volume of Suds (ml) | |
|---|---|---|
|  | No Soil | 1% Soil* Present |
| Generic commercial product (Crystal White ®)** | 110 | 30 |
| Premium commercial product B (Palmolive Liquid ®) | 120 | 100 |
| Premium commercial product C (Joy ®) | 125 | 120 |
| 12% $C_{11.8}$ LAS/8% Ex. II's alkyl polyglucoside | 180 | 120 |
| 18% $C_{11.8}$ LAS/12% Ex. II's alkyl polyglucoside | 240 | 150 |
| 24% $C_{11.8}$ LAS/16% Ex. II's alkyl polyglucoside | 300 | 180 |

*Soil is added as described in Ex. VII.
**Crystal White ® is available from Colgate-Palmolive Co.
Palmolive Liquid ® is available from Colgate-Palmolive Co.
Joy ® is available from The Proctor & Gamble Company.

Suds generated as in Ex. I using a test solution containing 0.2% by wt. of the indicated commercial product or 0.2% of a product formulated with the surfactant mixtures shown.

As can be seen, the simple mixtures of surfactants representative of this invention can be formulated to be superior, or at least equal, to even the best light-duty dishwashing liquids.

EXAMPLE X

| Wt. % of: | A | B | C | D | E | F |
|---|---|---|---|---|---|---|
| $C_{11.8}$ LAS (Sodium) | 0 | 20 | 40 | 60 | 80 | 100 |
| Sucrose monolaurate | 100 | 80 | 60 | 40 | 20 | 0 |
| Relative Volume of suds (ml.) | 30 | 100 | 150 | 190 | 210 | 220 |

300 ppm of surfactant mixture used in test solution of Ex. I.

The above demonstrates that structures which are similar to the alkyl polyglucosides do not provide the benefits of this invention.

EXAMPLE XI

Shampoo

| | |
|---|---|
| Cocamido propyl betaine (30% aqueous solution) | 50.00% |
| Ex. I's alkyl polyglucoside | 5.00% |
| Polyethylene glycol distearate | 1.00% |
| Preservative | 0.03% |
| Distilled water   q.s. | 100.00% |

EXAMPLE XII

Shampoo

| | |
|---|---|
| Alpha-olefin sulfonate (40% aqueous solution) | 30.00% |
| Ex. I's alkyl polyglucoside | 3.00% |
| Hydroxyethyl cellulose | 0.80% |
| Perfume | 1.00% |
| Preservative | 0.04 |
| Distilled water   q.s. | 100.00% |

EXAMPLE XIII

Paraffin Sulfonate Suds Boosting

| Wt. % of: | A | B | C | D | E | F |
|---|---|---|---|---|---|---|
| Mixture of sodium $C_{14-15}$ paraffin sulfonate | 0 | 20 | 40 | 60 | 80 | 100 |
| $C_{12-15}G_{4-5}$* | 100 | 80 | 60 | 40 | 20 | 0 |
| Relative Vol. of Suds (ml) | 185 | 250 | 275 | 275 | 235 | 210 |

Test Conditions:
Total concentration of 300 ppm; water having 8 grains of mixed hardness.
*$C_{12-15}G_{4-5}$ is a notation for an alkyl polysaccharide surfactant in which there are 4–5 glucoside units and in which the alkyl group has 12–15 carbons.

EXAMPLE XIV

Sodium vs. Magnesium Alkylbenzene Sulfonate

| | Relative Volume of Suds (ml.) | | |
|---|---|---|---|
| | Without Soil | With Soil* | |
| | | 0.6% | 1.0% |
| 0.2% aqueous solution of a detergent composition with: | | | |
| 15% Ex. II's alkyl polyglucoside; 22% $C_{11.8}$ alkylbenzene sulfonate with the benzene group attached primarily to the center of the alkyl chain, sodium neutralized | 450 | 150 | 75 |
| 15% Ex. II's alkyl polyglucoside; 22% $C_{11.8}$ alkylbenzene sulfonate with the benzene group attached primarily to the center of the alkyl chain, magnesium neutralized | 450 | 200 | 110 |
| Premium product (Joy ®) | 350 | 120 | 75 |

*Soil added to the test solution as in Ex. VIII.

EXAMPLE XV

The optimum alkylpolysaccharides, especially alkylpolyglucosides have an HLB* of from about 6 to about 27 and a critical micelle concentration (CMC)** of less than about 1000 ppm, preferably less than about 500. Short chain alkylpolysaccharides in which the alkyl group contains less than about 8 carbon atoms have unacceptably high CMC's and those alkylpolysaccharides having more than about 4 saccharide units have unacceptably high HLB's as is shown in the following table in which the alkyl group and the glucoside chain length were varied.

| # of Carbons | # of Glucosides | $G_0$ | $G_1$ | $G_2$ | $G_3$ | $G_4$ | $G_5$ |
|---|---|---|---|---|---|---|---|
| $C_4$ | HLB | 5.1 | 12.4 | 17.9 | 23.3 | 28.8 | 34.2 |
| $C_6$ | HLB | 4.2 | 11.4 | 17.0 | 22.4 | 27.8 | 33.2 |
| $C_8$ | HLB | 3.2 | 10.5 | 16.0 | 21.4 | 26.9 | 32.3 |
| | CMC | | ~7000 | | | | |
| $C_{10}$ | HLB | 2.2 | 9.6 | 15.0 | 20.4 | 26.0 | 31.4 |
| | CMC | | ~700 | 2000E | | | |
| $C_{12}$ | HLB | 1.3 | 8.6 | 14.1 | 19.5 | 25.0 | 30.4 |
| | CMC | ~6.0 | ~70 | ~200 | 225E | | ~250 |
| $C_{14}$ | HLB | 0.4 | 7.6 | 13.2 | 18.6 | 24.0 | 29.4 |
| | CMC | | ~6 | ~20 | 25-60E | | |
| $C_{16}$ | HLB | 0.0 | 6.7 | 12.2 | 17.6 | 23.1 | 28.5 |
| | CMC | ~0.3 | ~0.6 | ~4 | | | |
| $C_{18}$ | HLB | 0.0 | 5.8 | 11.2 | 16.6 | 22.2 | 27.6 |
| | CMC | | ~1 | | | | |

E = Estimated
*HLB determined according to Davies:Proc. & International Congress, Surface Activity 1,426, Butterworths, London, 1957.
**ppm As can be seen above, (1) longer pure glucoside chain lengths raise the HLB and lower the molecule's surface activity (high CMC) and (2) the shorter alkyl chain lengths have extremely high CMC's even as the monoglucoside.

EXAMPLE XVI

The following formulas were prepared:

| | A | B | C |
|---|---|---|---|
| Magnesium linear $C_{11.2}$ alkylbenzene sulfonate | 22.4 | 22.4 | 22.4 |
| $C_{12-13}$ alkylpolyglucoside ($G_{1.7}$) (<2% free fatty alcohol) | 14.9 | 14.9 | 14.9 |
| $C_{9-11}$ alkoxypropyldihydroxyethyl amine oxide | — | 4 | — |
| $C_{12}$ alkyldihydroxy ethyl amine oxide | — | — | 4 |
| Ethanol | 5 | 5 | 5 |

-continued

|  | A | B | C |
|---|---|---|---|
| Water | balance | balance | balance |

Formulas A, B and C were compared by generating suds with a constant source of agitation under standard conditions (1 gal. water, 115° F. (46.1° C.) 7 gr. hardness in a 3 gal. dishpan using a standardized mixture of fat plus protein, carbohydrate and edible acid). Dinner plates are washed with 4 ml. of soil on each plate and the suds height is measured after each five plates. 30 plates in total are washed and the integral of the suds height taken over the number of plates washed is reported as the SDW grade (SDW=Suds During Washing).

|  | A | B | C |
|---|---|---|---|
| SDW grade | 24 | 28.8 | 28.4 |

This shows that the addition of a small amount of these amine oxides dramatically increases the amount of dishes that can be washed. Similar results are obtained when a fatty acid amide, e.g., a coconut fatty acid amide, diethanol amide, and/or isopropanol amide is substituted, at least in part for the specific amine oxides.

EXAMPLE XVII 105 grams of sodium dodecylbenzene sulfonate are mixed with 350 grams of anhydrous sodium sulfate. After the mixture is ground into a fine powder, 70 g of $C_{12-13}$ alkylpolyglucoside ($G_{2.2}$) (<2% free fatty alcohol) are then mixed in. The mixture is transferred into a fluid bed dryer operated at room temperature (e.g., Aeromatic Inc., Model STREA-1), then 100 grams of a 50% solution of said alkylpolyglucoside is sprayed onto the powder. 7.5 milliliters of a 1% polar blue solution are sprayed onto the powder and a small portion of perfume is then added. The resulting granule is dried in a vacuum oven at 30 in. of Hg vacuum at 50° C. for ten hours to remove excess water.

In a similar manner 60 grams of a 50% solution of said alkylpolyglucoside is sprayed onto 100 gram of Berkite and 50 grams of sodium dodecylbenzene sulfonate flakes are admixed with the product to give a light duty granule.

EXAMPLE XVIII

Ammonium $C_{11.2}$ linear alkyl benzene sulfonate was admixed with $C_{12}$ alkylpolyglucoside $G_{3.5}$ in a ratio of about 2:1. The mixture was used at a level of 400 ppm in city water. The initial suds volume was more than 300 ml., but after the addition of about 1.25 grams of a standard grease soil per 200 ml. of wash solution, the suds had disappeared. Substitution of a sodium $C_{12-16}$ alkyl glyceryl ether sulfonate for 25% and 40% of the mixture extended the point at which there was no suds to 1.5 and 1.75 grams of soil per 200 ml. of wash solution respectively.

Similar results are obtained when a sodium, potassium, ammonium, or monoethanolammonium $C_{12-16}$ alkylpolyethoxy$_3$ acetate, or $C_{14-16}$ olefin sulfonate or mixtures thereof is substituted for at least part of the alkyl glyceryl ether sulfonate.

EXAMPLE XIX

The following formula was prepared with alkylpolyglucosides having 0.3% and 1% free fatty alcohol respectively.

|  | Wt. % |
|---|---|
| Ammonium $C_{11.2}$ linear alkyl benzene sulfonate | 17.5 |
| Magnesium $C_{11.2}$ linear alkyl benzene sulfonate | 6.4 |
| Ammonium $C_{12-13}$ alkyl polyethoxylate (0.8) sulfate | 6.1 |
| $C_{12-13}$ alkylpolyglucoside $G_{1.7}$ | 5 |
| Minors and water | balance |

The SDW values for the low and high alcohol samples were 12.9 and 12.2 respecively with an $LSD_{0.05}$ at 0.6. See Ex. XVI for test method.

EXAMPLE XX

The following formulas were prepared:

|  | % by weight | | | |
|---|---|---|---|---|
|  | A | B | C | D |
| Ammonium/magnesium $C_{11.2}$ linear alkyl benzene sulfonate | 24.2 | 21.8 | — | — |
| Ammonium/magnseium $C_{12-15}$ olefin sulfonate | — | — | 12.8 | 10.6 |
| Ammonium/magnesium $C_{12-13}$ alkyl sulfonate | — | — | 19.2 | 15.9 |
| Ammonium $C_{12-13}$ alkyl polyethoxylate (0.8) sulfate | 6.5 | 5.8 | — | — |
| $C_{12}$ fatty acid diethanolamide | — | 3.8 | — | 5.5 |
| $C_{12-13}$ alkylpolyglucoside $G_{1.7}$ (free fatty alcohol <0.5%) | 5.3 | 4.8 | 4 | 3.3 |
| Minors and water | balance | | | |
| The SDW Index | 79 | 89 | 97 | 107 |

The SDW index is the SDW grade for each product as a percentage of the SDW value of a standard commercial product.

The following are examples of particularly preferred compositions. The broad and preferred ranges of ingredients which can be used are given in the second and third columns, respectively, in each example.

EXAMPLE XXI

|  | % by Weight | | |
|---|---|---|---|
| Ammonium $C_{11.4}$ alkyl benzene sulfonate | 17.5 | 10–35 | 12–25 |
| Magnesium $C_{11.4}$ alkyl benzene sulfonate | 6.4 | 0–11 | 3–9 |
| Ammonium $C_{12-13}$ alkyl polyethoxylate (0.8) sulfates | 6.1 | 2–11 | 3–9 |
| $C_{12-13}$ alkyl polyglucoside (1.7) derived from glucose (<0.5% free fatty alcohol) | 5.0 | 2–11 | 2–7 |
| Ethanol | 3.7 | 0–10 | 0–5 |
| Ammonium xylene sulfonate | 3.0 | 0–10 | 0–5 |
| H$_2$O & minor components, e.g., perfume | Balance | | |

EXAMPLE XXII

| | % by Weight | | |
|---|---|---|---|
| Ammonium $C_{12-13}$ alkyl sulfate | 15.7 | 7-23 | 10-20 |
| Sodium $C_{14-16}$ olefin sulfonate | 10.4 | 4-19 | 6-13 |
| $MgCl_2.6H_2O$ | 5.6 | 0-11 | 2-10 |
| Coconut monoethanol amide | 5.5 | 2-8 | 3-7 |
| $C_{12-13}$ alkyl polyglucoside (1.7) derived from glucose (<0.5% free fatty alcohol) | 5.9 | 2-12 | 3-9 |
| Ethanol | 4.0 | 0-10 | 0-10 |
| $H_2O$ and minor components, e.g., perfume | | Balance | |

The alkyl groups in the surfactants of Examples XXI and XXII can vary from about 10 to about 16 carbon atoms and the cations can be ammonium, sodium, potassium, monoethanolammonium, diethanolammonium, triethanolammonium, magnesium, or preferably, mixtures thereof. Any of the preferred alkyl polyglycosides can be used and other known amine oxide and amide suds boosters disclosed herein can be used.

EXAMPLE XXIII

When a 2:1 mixture of an ammonium $C_{11.2}$ alkylbenzene sulfonate and the $C_{12-13}$ alkylpolyglucoside (2-4) (>2% free fatty alcohol) are tested under the conditions of Example II the initial suds volume is good, but the SDW grade is not as good as some premium commercial products. Substitution of between 25% and 50% of the mixture with a sodium $C_{12-16}$ alkyl glyceryl ether sulfonate, or sodium $C_{14-16}$ olefin sulfonate, or sodium $C_{12-13}$ alkyl polyethoxylate$_{(3)}$ acetate increases the SDW grade without lowering the initial sudsing excessively.

Known analytical techniques can be used to determine the structures of the alkylpolysaccharide surfactants herein; for example, to determine the glycosidic chain length, the amount of butyl glucoside, the free fatty alcohol content, and the level of unreacted polysaccharide. More specifically, gas or liquid chromatography can be used to determine the unreacted alcohol content and the unreacted polysaccharide content respectively. Proton nmr can be used to determine the average glycosidic chain length. The point of attachment of the hydrophilic portion of the molecule to the hydrophobic portion of the molecule can be determined by $^{13}C$ nmr.

The alkylpolysaccharide surfactants are complex mixtures. Their components vary depending upon the nature of the starting materials and the reaction by which they are prepared. Analytical standards which are useful in calibrating instruments for analyzing the components of a particular alkylpolysaccharide surfactant can be obtained from Calbiochem Behring Co. LaJolla, Calif. These standards include those for octylglucoside (Calbiochem #494559), decylglucoside (Calbiochem #252715), dodecylmaltoside (Calbiochem #3243555).

The HLBs of alkylpolysaccharide surfactants useful in the foaming compositions of this invention have the values given in EXAMPLE XV; the CMCs will approximate those values given in the same example. Alkylpolysaccharide surfactants having the structures specified in the claims and characterized by one or more of the standard analytical techniques will give the results indicated in the examples.

What is claimed is:
1. A foaming composition comprising
    (1) an alkylpolysaccharide surfactant having the formula $RO(R^1O)_t(Z)_x$ where Z is a moiety derived from a reducing saccharide containing from 5 to 6 carbon atoms and wherein R is a hydrophobic group selected from the group consisting of alkyl, alkylphenyl, hydroxyalkylphenyl and hydroxyalkyl groups and mixtures thereof in which said alkyl groups contain from about 8 to about 20 carbon atoms; $R^1$ contains from 2 to about 4 carbon atoms; t is from 0 to about 30; and x is a number from about 1.5 to about 10;
    (2) an anionic cosurfactant selected from the group consisting of sulfates, sulfonates, carboxylates and mixtures thereof, neutralized with one or more cationic moieties,
the ratio of (2) to (1) being from about 1:10 to about 10:1 except that when the cosurfactant is an alkylbenzene sulfonate, the ratio of (2) to (1) is at least about 1:2, and when the cosurfactant is soap the ratio of (2) to (1) is at least about 1:2, and when the anionic cosurfactant does not contain a sulfonate or carboxylate x must be from 1.5 to 3 and the alkylpolysaccharide surfactant must have a free fatty alcohol content of less than about 2% by weight.

2. The composition of claim 1 wherein the cosurfactant is selected from the group consisting of alkylbenzene sulfonates, alphaolefin sulfonates, alkyl sulfates and paraffin sulfonates and wherein the cationic moiety is selected from the group consisting of sodium, potassium, ammonium, monoethanolammonium, diethanolammonium, triethanolammonium, calcium, magnesium and mixtures thereof.

3. The composition of claim 2 wherein the cosurfactant is an alkylbenzene sulfonate.

4. The composition of claim 3 wherein the phenyl portion of the alkylbenzene sulfonate is attached near the middle of the alkyl chain and the cationic moiety is magnesium.

5. The composition of claim 2 wherein the cosurfactant is an alpha-olefin sulfonate.

6. The composition of claim 2 wherein the cosurfactant is a paraffin sulfonate.

7. The composition of claim 1 wherein the anionic cosurfactant has the formula

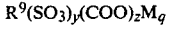

$$R^9(SO_3)_y(COO)_zM_q$$

wherein $R^9$ is an alkyl, alkylphenyl, hydroxyalkylphenyl or hydroxylalkyl or mixtures thereof, said alkyl groups containing from 6 to 30 carbon atoms; wherein y is a number from 0 to 4, z is a number from 0 to 4, y+z is at least 1 and wherein M is a cationic moiety with q being selected to complete the formula.

8. The composition of claim 7 wherein y is 0; z is 1; and wherein the cationic moiety is selected from the group consisting of sodium, potassium, ammonium, monoethanolammonium, diethanolammonium, triethanolammonium, calcium, magnesium and mixtures thereof.

9. The composition of any one of claims 1-8 wherein x is a number from 1.5 to 4.

10. The composition of claim 7 wherein $R^9$ contains a quaternary ammonium group, y+z is equal to 1, and q is equal to 0.

* * * * *

REEXAMINATION CERTIFICATE (2258th)

United States Patent [19]

Llenado

[11] B1 4,565,647

[45] Certificate Issued Apr. 5, 1994

[54] FOAMING SURFACTANT COMPOSITIONS

[75] Inventor: Ramon A. Llenado, West Chester, Ohio

[73] Assignee: The Procter & Gamble Company, Cincinnati, Ohio

Reexamination Requests:
No. 90/002,719, May 7, 1992
No. 90/002,945, Feb. 1, 1993

Reexamination Certificate for:
Patent No.: 4,565,647
Issued: Jul. 12, 1982
Appl. No.: 395,751
Filed: Jan. 21, 1986

[*] Notice: The portion of the term of this patent subsequent to Aug. 2, 2000, has been disclaimed.

Related U.S. Application Data

[63] Continuation-in-part of Ser. No. 371,747, Apr. 26, 1982, abandoned, and Ser. No. 282,976, Jul. 13, 1981, abandoned.

[51] Int. Cl.$^5$ .................. B01F 17/02; B01F 17/12; B01F 17/56; B01J 13/00
[52] U.S. Cl. .................................. 252/354; 47/2; 209/20; 252/3; 252/121; 252/174.17; 252/307; 252/353; 252/355; 252/555; 252/DIG. 10; 252/DIG. 13; 252/DIG. 14; 427/244; 507/110
[58] Field of Search .................. 252/3, 307, 353, 354, 252/174.17, DIG. 10, DIG. 14; 427/244

[56] References Cited

U.S. PATENT DOCUMENTS

| | | | |
|---|---|---|---|
| 3,219,656 | 11/1965 | Boettner | 536/18.3 |
| 3,721,633 | 3/1973 | Ranauto | 252/527 |
| 3,925,224 | 12/1975 | Winston | 252/89 |
| 4,019,998 | 4/1977 | Benson et al. | 252/135 |

FOREIGN PATENT DOCUMENTS

| | | |
|---|---|---|
| 135330 | 4/1933 | Austria . |
| 593422 | 2/1934 | Fed. Rep. of Germany . |
| 976088 | 11/1964 | United Kingdom . |
| 2050165A | 1/1981 | United Kingdom . |

OTHER PUBLICATIONS

Chemiker Ziegung 99, 1975, pp. 168–175.
CID, Chimie, Physique et Applications Pratiques des Agents de Surface, vol. III, pp. 211–217 (1969).
Shell Chemical Company Technical Bulletin SC:376–79 (1979).
Rohm & Haas Technical Bulletin Triton CG-110, May 1975.
Rivista Italiana, Oct. 1974, pp. 567–572.

*Primary Examiner*—Richard D. Lovering

[57] ABSTRACT

Foaming compositions containing an alkylpolysaccharide surfactant and a sulfate, sulfonate and/or carboxylate cosurfactant and processes for utilizing foams containing these compositions.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

Claims 1-9 and 10 are cancelled.

New claims 11-22 and 23 are added and determined to be patentable.

11. A foaming composition selected from the group consisting of dishwashing compositions, hairwashing compositions, laundry compositions, soap bars, bubble baths and shaving creams, the composition comprising (1) an alkylpolysaccharide surfactant having the formula $RO(R^1O)_t(Z)_x$ where Z is glucose, R is a hydrophobic group selected from the group consisting of alkyl, alkylphenyl, hydroxyalkylphenyl and hydroxyalkyl groups and mixtures thereof in which said alkyl groups contain from about 12 to about 20 carbon atoms; $R^1$ contains from 2 to about 4 carbon atoms; t is from 0 to about 30; and x is a number from about 1.5 to 4;

(2) an anionic cosurfactant selected from the group consisting of sulfates, sulfonates, carboxylates and mixtures thereof, neutralized with one or more cationic moieties, the ratio of (2) to (1) being from about 1:10 to about 10:1 except that when the cosurfactant is an alkyl benzene sulfonate, the ratio of (2) to (1) is at least about 1:2, and when the cosurfactant is soap the ratio of (2) to (1) ranges from about 1:2 to 4:1, and when the anionic cosurfactant does not contain a sulfonate or carboxylate x must be from about 1.5 to 3 and the alkylpolysaccharide surfactant must have a free fatty alcohol content of less than about 2% by weight.

12. The composition of claim 11 wherein t is from 0 to about 10.

13. The composition of claim 12 wherein t is 0.

14. The composition of claim 11 selected from the group consisting of dishwashing compositions, hairwashing compositions, and laundry compositions.

15. The composition of claim 12 which is a light duty liquid dishwashing composition.

16. The composition of claim 11 wherein the cosurfactant is selected from the group consisting of alkylbenzene sulfonates, alphaolefin sulfonates, alkyl sulfates and paraffin sulfonates and wherein the cationic moiety is selected from the group consisting of sodium, potassium, ammonium, monoethanolammonium, diethanolammonium, triethanolammonium, calcium, magnesium and mixtures thereof.

17. The composition of claim 16 wherein the cosurfactant is an alkylbenzene sulfonate.

18. The composition of claim 17 wherein the phenyl portion of the alkylbenzene sulfonate is attached near the middle of the alkyl chain and the cationic moiety is magnesium.

19. The composition of claim 16 wherein the cosurfactant is an alpha-olefin sulfonate.

20. The composition of claim 16 wherein the cosurfactant is a paraffin sulfonate.

21. The composition of claim 11 wherein the anionic cosurfactant has the formula $$R^9(SO_3)_y(COO)_zM_q$$

wherein $R^9$ is an alkyl, alkylphenyl, hydroxyalkylphenyl or hydroxyalkyl or mixtures thereof, said alkyl groups containing from 6 to 30 carbon atoms; wherein y is a number from 0 to 4, z is a number from 0 to 4, y+z is at least 1 and wherein M is a cationic moiety with q being selected to complete the formula.

22. The composition of claim 21 wherein y is 0; z is 1; and wherein the cationic moiety is selected from the group consisting of sodium, potassium, ammonium, monoethanolammonium, diethanolammonium, triethanolammonium, calcium, magnesium and mixtures thereof.

23. The composition of claims 11 wherein x is a number which is no greater than 2.7.

* * * * *